United States Patent [19]

Harris et al.

[11] Patent Number: 5,763,361
[45] Date of Patent: Jun. 9, 1998

[54] 17-ALKYL-7-SUBSTITUTED-4-AZA STEROID DERIVATIVES AS 5-α-REDUCTASE INHIBITORS

[75] Inventors: Georgianna Harris, Tinton Falls; Richard L. Tolman, Warren; Soumya P. Sahoo, Old Bridge, all of N.J.

[73] Assignee: Merck & Co., Inc., Rahway, N.J.

[21] Appl. No.: 734,705

[22] Filed: Oct. 21, 1996

Related U.S. Application Data

[60] Provisional application No. 60/005,832, Oct. 23, 1995.

[51] Int. Cl.[6] ............................................. A61K 31/58
[52] U.S. Cl. ................................................ 514/284; 546/77
[58] Field of Search ............................... 514/284; 546/77

[56] References Cited

U.S. PATENT DOCUMENTS

| | | | |
|---|---|---|---|
| 3,239,417 | 3/1966 | Di Tullio et al. | 546/77 |
| 3,264,301 | 8/1966 | Doorenbos et al. | 546/77 |
| 4,220,775 | 9/1980 | Rasmusson et al. | 546/77 |
| 4,377,584 | 3/1983 | Rasmusson et al. | 514/284 |
| 4,760,071 | 7/1988 | Rasmusson et al. | 514/284 |
| 5,237,064 | 8/1993 | Bakshi et al. | 546/77 |
| 5,359,071 | 10/1994 | Durette et al. | 546/78 |
| 5,470,976 | 11/1995 | Humphrey et al. | 546/77 |
| 5,494,914 | 2/1996 | Labrie | 514/284 |
| 5,512,555 | 4/1996 | Waldstreicher | 514/284 |
| 5,516,779 | 5/1996 | Von Langen et al. | 514/284 |
| 5,527,807 | 6/1996 | Bakshi et al. | 514/284 |
| 5,543,417 | 8/1996 | Waldstreicher | 514/284 |
| 5,585,383 | 12/1996 | Forman et al. | 546/77 |
| 5,658,922 | 8/1997 | Durette et al. | 514/284 |

FOREIGN PATENT DOCUMENTS

| | | |
|---|---|---|
| 0 004 949 | 10/1979 | European Pat. Off. . |
| 0 572 166 | 12/1993 | European Pat. Off. . |
| WO 92/16233 | 10/1992 | WIPO . |
| WO 93/23039 | 11/1993 | WIPO . |
| WO 93/23376 | 11/1993 | WIPO . |
| WO 93/23419 | 11/1993 | WIPO . |
| WO 95/00147 | 5/1995 | WIPO . |
| WO 95/13815 | 5/1995 | WIPO . |
| WO 95/32215 | 11/1995 | WIPO . |

OTHER PUBLICATIONS

Back et al., Can. J. Chem. 69 (1991), pp. 1482–1486, "The synthesis of some novel N–chloro–delta1–4–azasteroids by efficient N–chlorination of azasteroid lactams . . .".
Rasmusson et al., J. Med. Chem. 27 (1984), pp. 1690–1701, "Azasteroids as inhibitors of rat prostatic 5alpha–reductase".
Back et al., J. Org. Chem. 54 (1989), pp. 1904–1910, "N–Chloroazasteroids: A novel class of reactive steroid analogues".
Brooks et al., Steroids 47/1 (1986), pp. 1–19, "5alpha–reductase inhibitory and anti–androgenic activities of some 4–azasteroids in the rat".
The Daily, Tuesday, May 7, 1996, "New data on Proscar, Abbotts's Hytrin show conflicting results".
Wall Street Journal, May 7, 1996, p. B4, "Study finds Abbott's prostate drug is much more effective than Merck's".
Boyle et al., Urology 48:398–405, 1996, "Prostate volume predicts outcome of treatment of benign prostatic hyperplasia with finasteride".
Diani et al J. Clin. Endocrin. and Metab. vol. 55 No. 1 pp. 345–350, 1990.
Heluker, Wall St. Jour. pp. A1, A7, 7 Jun. 1991.
Stinson Chem and Eng News, Jun. 29, 1992 pp. 7–8.

*Primary Examiner*—Donald G. Daus
*Attorney, Agent, or Firm*—Catherine D. Fitch; Melvin Winokur

[57] ABSTRACT

The novel compounds of the present invention are those of structural formula I:

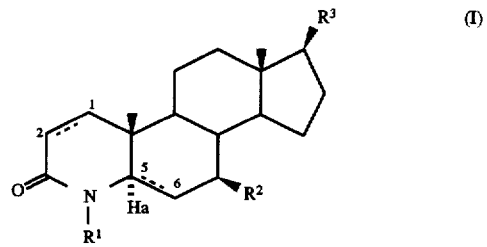

(I)

or a pharmaceutically acceptable salt, or stereoisomer thereof, which are inhibitors of 5α-reductase, particularly 5α-reductase type 1. The compounds of formula I are useful in the systemic, including oral, or parenteral or topical treatment of hyperandrogenic conditions such as acne vulgaris, seborrhea, androgenic alopecia which includes female and male pattern baldness, female hirsutism, benign prostafic hyperplasia, and the prevention and treatment of prostatic carcinoma, as well as in the treatment of prostatitis. Methods of using the compounds of formula I for the treatment of hyperandrogenic conditions such as acne vulgaris, seborrhea, androgenic alopecia, male pattern baldness, female hirsutism, benign prostatic hyperplasia, and the prevention and treatment of prostatic carcinoma, as well as the treatment of prostatitis are provided, as well as pharmaceutical compositions for the compounds of formula I. The use of compounds of formula I in combination with other, active agents, for example with a 5α-reductase type 2 inhibitor such as finasteride or epristeride, or a potassium channel opener, such as minoxidil, or a retinoic acid or a derivative thereof is also taught, wherein such combinations would be useful in one or more of the above-mentioned methods of treatment or pharmaceutical compositions.

12 Claims, No Drawings

17-ALKYL-7-SUBSTITUTED-4-AZA STEROID DERIVATIVES AS 5-α-REDUCTASE INHIBITORS

CROSS-REFERENCE TO RELATED APPLICATIONS

This is a non-provisional application based on Provisional application, Ser. No. 60/005,832, filed Oct. 23, 1995 (now abandoned).

FIELD OF THE INVENTION

The present invention provides novel compounds, novel compositions, methods of their use and methods of their manufacture, where such compounds are generally pharmacologically useful as agents in therapies whose mechanism of action rely on the inhibition of 5α-reductase, most particularly the isozyme 5α-reductase type 1.

BACKGROUND OF THE INVENTION

Certain undesirable physiological manifestations, such as acne vulgaris, seborrhea, female hirsutism, androgenic alopecia which includes female and male pattern baldness, and benign prostatic hyperplasia, are the result of hyperandrogenic stimulation caused by excessive accumulation of testosterone ("T") or similar androgenic hormones in the metabolic system. Androgenic alopecia is also known as androgenetic alopecia. Early attempts to provide a chemotherapeutic agent to counter the undesirable results of hyperandrogenicity resulted in the discovery of several steroidal antiandrogens having undesirable hormonal activities of their own. The estrogens, for example, not only counteract the effect of the androgens but have a feminizing effect as well. Non-steroidal antiandrogens have also been developed, for example, 4'-nitro-3'-trifluoromethyl-isobutyranilide. See Neri, et al., Endocrinol. 1972, 91 (2). However, these products, though devoid of hormonal effects, compete with all natural androgens for receptor sites, and hence have a tendency to feminize a male host or the male fetus of a female host and/or initiate feed-back effects which would cause hyperstimulation of the testes.

The principal mediator of androgenic activity in some target organs, e.g. the prostate, is 5a-dihydrotestosterone ("DHT"), formed locally in the target organ by the action of testosterone-5α-reductase. Inhibitors of testosterone-5α-reductase will serve to prevent or lessen symptoms of hyperandrogenic stimulation in these organs. See specially U.S. Pat. Nos. 4,377,584, issued Mar. 22, 1983, and 4,760,071, issued Jul. 26, 1988, both assigned to Merck & Co., Inc.

The enzyme 5α-reductase catalyzes the reduction of testosterone to the more potent androgen, dihydrotestosterone, as shown below:

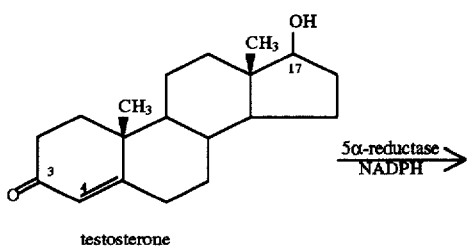

testosterone

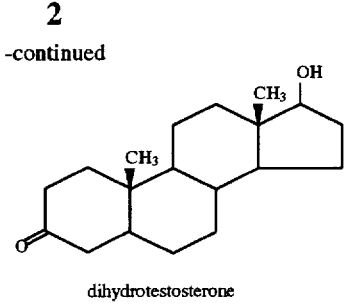

dihydrotestosterone

Finasteride, (17β-(N-tert-butylcarbamoyl)-3-oxo-4-aza-5α-androst-1-ene-3-one) as shown below, is a potent inhibitor of the human prostate enzyme.

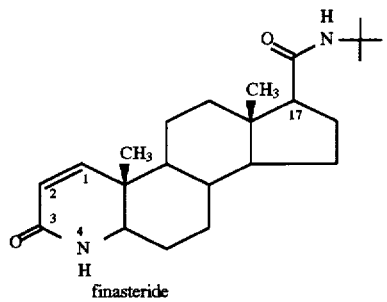

finasteride

Under the trade name PROSCAR®, finasteride is known to be useful in the treatment of hyperandrogenic conditions; see eg. U.S. Pat. No. 4,760,071. Finasteride is currently prescribed for the treatment of benign prostatic hyperplasia (BPH), a condition afflicting to some degree the majority of men over age 55. Finasteride's utility in the treatment of androgenic alopecia and prostatic carcinoma is also disclosed in the following documents: EP 0 285,382, published 5 Oct. 1988; EP 0 285,383, published 5 Oct. 1988; Canadian Patent no. 1,302,277; and Canadian Patent no. 1,302,276.

There are two isozymes of 5α-reductase in humans. One isozyme (type 1 or 5α-reductase 1) predominates in sebaceous glands of facial and skin tissue and is relatively insensitive to finasteride (see, e.g., G. Harris, et al., Proc. Natl. Acad. Sci. USA, Vol. 89, pp. 10787–10791 (November 1992)); the other (type 2 or 5α-reductase 2) predominates in the prostate and is potently inhibited by finasteride.

Since 5α-reductase and its isozymes convert testosterone to DHT, inhibition of either or both of the isozymes would serve to alleviate the conditions and diseases mediated by DHT. The present invention addresses this by providing novel compounds that are active as inhibitors of 5α-reductase, and are particularly potent inhibitors of 5α-reductase type 1.

SUMMARY OF THE INVENTION

The novel compounds of this invention have the structural formula I:

3

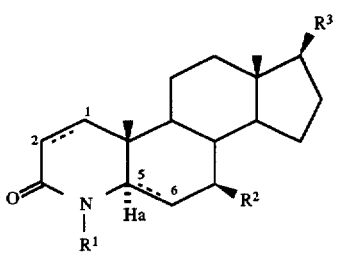

wherein:
the C1–C2 and C5–C6 bonds designated with a dotted line each independently represent a single or double bond, provided that when the C5–C6 is a double bond, $H_a$ is absent and when the C5–C6 bond is a single bond Ha is present and represents hydrogen;

$R^1$ is selected from hydrogen and $C_{1-5}$ alkyl;

$R^2$ is $C_{1-5}$alkyl, either straight or branched chain; and $R^3$ is $C_{3-7}$alkyl, either straight or branched chain, optionally having one degree of unsaturation;

or a pharmaceutically acceptable salt, or stereoisomer thereof, which are inhibitors of 5α-reductase, particularly 5α-reductase type 1. The compounds of formula I are useful in the systemic, including oral, parenteral or topical treatment of hyperandrogenic conditions such as acne vulgaris, seborrhea, androgenic alopecia which includes female and male pattern baldness, female hirsutism, and benign prostatic hyperplasia, as well as in the treatment of prostatitis.

Therefore it is an object of this invention to provide compounds that have sufficient activity in the inhibition of 5α-reductase, particularly 5α-reductase type 1. It is an additional object of this invention to provide methods of using the compounds of formula I for the treatment of hyperandrogenic conditions such as acne vulgaris, seborrhea, androgenic alopecia, male pattern baldness, female hirsutism, and benign prostatic hyperplasia, as well as the treatment of prostatitis. It is a further object of this invention to provide pharmaceutical compositions for the compounds of formula I. Another object of this invention is to provide compounds of formula I in combination with other active agents, for example with finasteride, or a potassium channel opener, such as minoxidil, or a retinoic acid or a derivative thereof, wherein such combinations would be useful in one or more of the above-mentioned methods of treatment or pharmaceutical compositions.

DETAILED DESCRIPTION OF THE INVENTION

The novel compounds of the present invention are those of structural formula I:

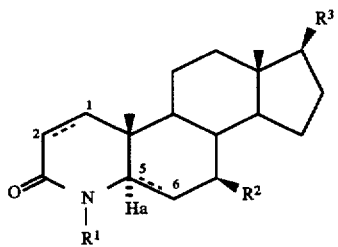

wherein:
the C1–C2 and C5–C6 bonds designated with a dotted line each independently represent a single or double bond, provided that when the C5–C6 is a double bond, Ha is absent and when the C5–C6 bond is a single bond Ha is present and represents hydrogen;

4

$R^1$ is selected from hydrogen and $C_{1-5}$ alkyl;

$R^2$ is $C_{1-5}$alkyl, either straight or branched chain; and $R^3$ is $C_{3-7}$alkyl, either straight or branched chain, optionally having one degree of unsaturation;

or a pharmaceutically acceptable salt, or stereoisomer thereof, which are inhibitors of 5α-reductase, particularly 5α-reductase type 1.

In one class of the instant invention are compounds of formula I wherein the C5–C6 bond is a single bond and $H_a$ is present.

In a sub-class of the compounds of this class are compounds wherein $R^2$ is methyl.

Compounds illustrating this sub-class are:
7β,20-dimethyl-4-aza-5α-pregn-17-en-3-one,
7β,20-dimethyl-4-aza-5a-pregn-1,1 7-dien-3 -one,
20-ethyl -4,7β-dimethyl-4-aza-5α-pregn-1 7-en-3-one,
20-ethyl-4,7β-dimethyl-4-aza-5α-pregnan-3 -one,
7β,20-dimethyl-4-aza-5α-pregnan-3-one,
7β,20-dimethyl-4-aza-5α-pregn-1-en-3-one,
20-ethyl-4,7β-dimethyl-4-aza-5α-pregnan-3-one,
20-propyl -4,7β-dimethyl-4-aza-5α-pregnan-3 -one,
20-ethyl-4,7β-dimethyl-4-aza-5α-pregn-1-en-3-one,
4,7β,20-trimethyl-4-aza-5α-pregn-1-en-3-one,
20-propyl-4,7β,-dimethyl-4-aza-5α-pregn-1-en-3-one,
20-ethyl-7β-methyl-4-aza-5α-pregn-1-en-3-one,
20-propyl-7β-methyl-4-aza-5α-pregnan-3-one,
20-propyl-7β-methyl-4-aza-5α-pregn-1-en-3-one,
17β-n-propyl-7β-methyl-4-aza-5α-androst-1-en-3-one,
17β-n-propyl-4,7β-dimethyl-4-aza-5α-androst-1-en-3-one,
17β-n-butyl-7β-methyl-4-aza-5α-androst-1-en-3-one,
17β-isobutyl-7β-methyl4-aza-5α-androst-1-en-3-one,
17β-tert.-butyl-7β-methyl-4-aza-5α-androst-1-en-3-one,
17β-n-butyl-4,7β-dimethyl-4-aza-5α-androst-1-en-3-one,
17β-isobutyl-4,7β-dimethyl-4-aza-5α-androst-1-en-3-one,
17β-tert.-butyl-4,7β-dimethyl-4-aza-5α-androst-1-en-3-one,
17β-n-pentyl-7β-methyl-4-aza-5α-androst-1-en-3-one,
17β-isopentyl-7β-methyl-4-aza-5α-androst-1-en-3-one,
17β-(5-methylhexyl)-7β-methyl-4-aza-5α-androst-1-en-3-one,
17β-(5-methylhexyl)-4,7β-dimethyl-4-aza-5α-androst-1-en-3-one,
17β-n-propyl-7β-methyl-4-aza-5α-androstan-3-one,
17β-n-propyl-4,7β-dimethyl-4-aza-5α-androstan-3-one,
17β-n-butyl-7β-methyl-4-aza-5α-androstan-3-one,
17β-n-butyl-4,7β-dimethyl-4-aza-5α-androstan-3-one,
17β-(5-methylhexyl)-7β-methyl-4-aza-5α-androstan-3-one, and
17β-(5-methylhexyl)-4,7β-dimethyl-4-aza-5α-androstan-3-one.

Compounds further illustrating this sub-class are:
7β,20-dimethyl -4-aza-5α-pregn-17-en-3-one,
7β,20-dimethyl-4-aza-5α-pregn-1,17-dien-3-one,
20-ethyl-4,7β-dimethyl-4-aza-5α-pregn-17-en-3-one,
20-ethyl-4,7β-dimethyl-4-aza-5α-pregnan-3-one,
7β,20-dimethyl-4-aza-5α-pregnan-3-one,
7β,20-dimethyl-4-aza-5α-pregn-1-en-3-one,
20-ethyl-4,7β-dimethyl-4-aza-5α-pregnan-3-one,
20-propyl-4,7β-dimethyl-4-aza-5α-pregnan-3-one,
17β-n-propyl-7β-methyl-4-aza-5α-androst-1-en-3-one,
17β-n-butyl-7β-methyl-4-aza-5α-androst-1-en-3-one,
17β(5-methylhexyl)-7β-methyl-4-aza-5α-androst-1-en-3-one,
17β-n-propyl-7β-methyl-4-aza-5α-androstan-3-one,
17β-n-butyl-7β-methyl-4-aza-5α-androstan-3-one, and
17β-(5-methylhexyl)-7β-methyl-4-aza-5α-androstan-3-one.

In a further subclass of the present invention are compounds wherein the C1–C2 bond is a double bond and $R^1$ is hydrogen.

Compounds illustrating this subclass include:
7β,20-dimethyl-4-aza-5α-pregn-1,17-dien-3-one,
7β,20-dimethyl-4-aza-5α-pregn-1-en-3-one,
20-ethyl-7β-methyl-4-aza-5α-pregn-1-en-3-one,
20-propyl-7β-methyl-4-aza-5α-pregn-1-en-3-one,
17β-n-propyl-7β-methyl-4-aza-5α-androst-1-en-3-one,
17β-n-butyl-7β-methyl-4-aza-5α-androst-1-en-3-one,
17β-isobutyl-7β-methyl-4-aza-5α-androst-1-en-3-one,
17β-tert.-butyl-7β-methyl-4-aza-5α-androst-1-en-3-one,
17β-n-pentyl-7β-methyl-4-aza-5α-androst-1-en-3-one,
17β-isopentyl-7β-methyl-4-aza-5α-androst-1-en-3-one,
17β-(5-methylhexyl)-7β-methyl -4-aza-5α-androst-1-en-3-one.

In yet another subclass of this class of the present invention are compounds wherein $R^3$ is $C_{3-6}$ alkyl.

Compounds illustrating this sub-class are:
7β,20-dimethyl-4-aza-5α-pregn-17-en-3-one,
7β,20-dimethyl-4-aza-5α-pregn-1,17-dien-3-one,
20-ethyl-4,7β-dimethyl-4-aza-5α-pregn-17-en-3-one,
20-ethyl-4,7β-dimethyl-4-aza-5α-pregnan-3-one,
7β,20-dimethyl-4-aza-5α-pregnan-3-one,
7β,20-dimethyl-4-aza-5α-pregn-1-en-3-one,
20-ethyl -4,7β-dimethyl-4-aza-5α-pregnan-3-one,
20-propyl-4,7β-dimethyl-4-aza-5α-pregnan-3 -one,
20-ethyl-4,7β-dimethyl-4-aza-5α-pregn-1-en-3-one,
4,7β,20-trimethyl-4-aza-5α-pregn-1-en-3-one,
20-propyl-4,7β-dimethyl-4-aza-5α-pregn-1-en-3-one,
20-ethyl-7β-methyl-4-aza-5α-pregn-1-en-3-one,
20-propyl-7β-methyl-4-aza-5α-pregnan-3-one,
20-propyl-7β-methyl-4-aza-5α-pregn- 1-en-3-one,
17β-n-propyl-7β-methyl-4-aza-5α-androst-1-en-3-one,
17β-n-propyl-4,7β-dimethyl4-aza-5α-androst-1-en-3-one,
17β-n-butyl-7β-methyl-4-aza-5α-androst-1-en-3-one,
17β-isobutyl-7β-methyl-4-aza-5α-androst-1-en-3-one,
17β-tert.-butyl-7β-methyl-4-aza-5α-androst-1-en-3-one,
17β-n-butyl-4,7β-dimethyl-4-aza-5α-androst-1-en-3-one,
17β-isobutyl-4,7β-dimethyl4-aza-5α-androst-1-en-3-one,
171β-tert.-butyl-4,7β-dimethyl-4-aza-5α-androst-1-en-3-one,
171β-n-pentyl-7β-methyl-4-aza-5α-androst- 1-en-3-one,
17β-isopentyl-7β-methyl-4-aza-5α-androst- 1-en-3-one,
17β-(5-methylhexyl)-7β-methyl-4-aza-5α-androst-1-en-3 -one,
17β-(5-methylhexyl)-4,7p-dimethyl-4-aza-5α-androst-1-en-3-one,
17β-n-propyl-7β-methyl-4-aza-5α-androstan-3-one,
17β-n-propyl-4,7β-dimethyl-4-aza-5α-androstan-3-one,
17β-n-butyl-7β-methyl-4-aza-5α-androstan-3-one, and
17β-n-butyl-4,7β-dimethyl-4-aza-5α-androstan-3-one.

Further illustrating this subclass are compounds wherein $R^2$ is methyl.

In a further subclass of the present invention are compounds wherein the C1–C2 bond is a double bond, $R^1$ is hydrogen, $R^2$ is methyl, and $R^3$ is $C_{3-6}$ alkyl.

Compounds illustrating this subclass include:
7β,20-dimethyl-4-aza-5α-pregn-1,17-dien-3-one,
7,β,20-dimethyl-4-aza-5α-pregn-1-en-3-one,
20-ethyl-7β-methyl-4-aza-5α-pregn-1-en-3-one,
20-propyl-7β-methyl-4-aza-5α-pregn-1-en-3-one,
17β,-n-propyl-7β-methyl-4-aza-5α-androst-1-en-3-one,
17β,-n-butyl-7β-methyl-4-aza-5 α-androst-1-en-3-one,
17β-isobutyl-7β-methyl-4-aza-5α-androst-1-en-3-one,
17β-tert.-butyl-7β-methyl-4-aza-5α-androst-1-en-3-one,
17β-n-pentyl-7β-methyl-4-aza-5α-androst-1-en-3-one, and
17β-isopentyl-7β-methyl-4-aza-5α-androst-1-en-3-one.

Still further illustrating this subclass are compounds wherein $R^3$ is fully saturated.

Compounds illustrating this subclass include:
7β,20-dimethyl-4-aza-5α-pregn-1-en-3-one,
20-ethyl-7β-methyl-4-aza-5α-pregn-1-en-3-one,
20-propyl-7β-methyl-4-aza-5α-pregn-1-en-3-one,
17β-n-propyl-7β-methyl-4-aza-5α-androst-1-en-3-one,
17β-n-butyl-7β-methyl-4-aza-5α-androst-1-en-3-one,
17β-isobutyl-7β-methyl-4-aza-5α-androst-1-en-3-one,
17β-tert.-butyl-7β-methyl-4-aza-5α-androst-1-en-3-one,
17β-n-pentyl-7β-methyl-4-aza-5α-androst-1-en-3-one, and
17β-isopentyl-7β-methyl-4-aza-5α-androst-1-en-3-one.

In another class of the present invention are compounds wherein the C5–C6 bond is a double bond and $H_a$ is absent.

When any variable (e.g., alkyl, $R^2$, etc.) occurs more than one time in any constituent or in formula I, its definition on each occurrence is independent of its definition at every other occurrence. Also, combinations of substituents and/or variables are permissible only if such combinations result in stable compounds.

As used herein "alkyl" is intended to include both branched- and straight-chain saturated aliphatic hydrocarbon groups having the specified number of carbon atoms, e.g., methyl (Me), ethyl (Et), propyl, butyl, pentyl, and the isomers thereof such as isopropyl (i-Pr), isobutyl (i-Bu), secbutyl (s-Bu), tertbutyl (t-Bu), isopentane, etc.

The compounds of the present invention may be administered in the form of pharmaceutically acceptable salts. The term "pharmaceutically acceptable salt" is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations.

The compounds of the present invention may have chiral centers other than those centers whose stereochemistry is depicted in formula I, and therefore may occur as racemates, racemic mixtures and as individual enantiomers or diastereomers, with all such isomeric forms being included in the present invention as well as mixtures thereof. Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

The term "therapeutically effective amount" is that amount of a drug or pharmaceutical agent that will elicit the biological or medical response of a tissue, system, animal or human that is being sought by a researcher, veterinarian, medical doctor or other clinician, which includes alleviation of the symptoms of the disorder being treated.

More particularly, the present invention relates to a method for treating hyperandrogenic conditions in a mammal in need of such treatment comprising the administration to the mammal in need of such treatment of a therapeutically effective amount of a compound of the present invention. The novel methods of treatment of this invention are for disorders known to those skilled in the art. The term "mammal" includes humans. Preferably, the method of the present invention is for treating hyperandrogenic conditions in a human in need of such treatment.

Hyperandrogenic conditions treatable by the method of the present invention include benign prostatic hyperplasia, androgenic alopecia (including male pattern baldness, female pattern baldness and female hirsutism), acne vulgaris, seborrhea, and prostatitis.

The present invention has the objective of providing methods of treating hyperandrogenic conditions including androgenic alopecia, male pattern baldness, acne vulgaris, seborrhea, and female hirsutism by systemic, including oral, or parenteral or topical administration of the novel compounds of formula I either alone or in combination with a 5α-reductase 2 inhibitor, preferably selected from finasteride and epristeride, or a potassium channel opener, or a retinoic acid or derivative thereof. Alternatively, treatment may encompass administration of a combination of a compound of formula I with a 5α-reductase 2 inhibitor, preferably selected from finasteride and epristeride and another active agent such as a potassium channel opener, or a retinoic acid or derivative thereof. The term "treating androgenic alopecia" is intended to include the arresting and/or reversing of androgenic alopecia, and the promotion of hair growth.

The present invention has the further objective of providing methods of treating benign prostatic hyperplasia, and prostatitis, by oral, systemic or parenteral administration of the novel compounds of formula I either alone or in combination with a 5α-reductase 2 inhibitor, preferably selected from finasteride and epristeride. Alternatively, treatment may encompass administration of a combination of a compound of formula I with a 5α-reductase 2 inhibitor and/or another active agent such as an α1 or an α1$_a$ adrenergic receptor antagonist (α1$_a$ receptor antagonists were formerly called α1$_c$ receptor antagonists).

The present invention also has a further objective of providing methods of treating acne vulgaris, androgenic alopecia, seborrhea, female hirsutism, benign prostatic hyperplasia, and prostatitis, by oral, systemic, parental or topical administration of a combined therapy of a therapeutically effective amount of a compound of formula I with a therapeutically effective amount of an anti-androgen, such as, e.g., flutamide, spironolactone or casodex.

For combination treatment with more than one active agent, where the active agents are in separate dosage formulations, the active agents can be administered concomitantly, or they each can be administered at separately staggered times.

The present invention also has the objective of providing suitable topical, oral, systemic and parenteral pharmaceutical formulations for use in the novel methods of treatment of the present invention. The compositions containing the present compounds as the active ingredient for use in the treatment of the above-noted conditions can be administered in a wide variety of therapeutic dosage forms in conventional vehicles for systemic administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as an antiandrogenic agent.

The compounds of structural formula I useful in the present invention are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices may be administered systemically, by oral administration or by intravenous or intramuscular injection or topically.

For instance, for oral administration in the form of a tablet or capsule, the active drug component can be combined with an oral, non-toxic pharmaceutically acceptable inert carrier such as ethanol, glycerol, water and the like. Capsules containing the product of this invention can be prepared by mixing an active compound of the present invention with lactose and magnesium stearate, calcium stearate, starch, talc, or other carriers, and placing the mixture in gelatin capsules.

Tablets may be prepared by mixing the active ingredient with conventional tableting ingredients such as calcium phosphate, lactose, corn starch or magnesium stearate. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical pharmaceutical compositions may be, e.g., in the form of a solution, cream, ointment, gel, lotion, shampoo or aerosol formulation adapted for application to the skin. Topical pharmaceutical compositions useful in the method of treatment of the present invention may include about 0.001% to 0.1% of the active compound in admixture with a pharmaceutically acceptable carrier.

Topical preparations containing the active drug component can be admixed with a variety of carrier materials well known in the art, such as, e.g., alcohols, aloe vera gel, allantoin, glycerine, vitamin A and E oils, mineral oil, propylene glycol, PPG2 myristyl propionate, and the like, to form, e.g., alcoholic solutions, topical cleansers, cleansing creams, skin gels, skin lotions, and shampoos in cream or gel formulations. See, e.g., EP 0 285 382.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

The compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Preferably, doses of the compound of structural formula I useful in the method of the present invention range from 0.01 to 1000 mg per adult human per day. Most preferably, dosages range from 0.1 to 50 mg/day. For oral administration, the compositions are preferably provided in the form of tablets containing 0.01 to 1000 mg, particularly 0.01, 0.05, 0.1, 0.5, 1.0, 2.5, 5.0, 10.0, 15.0, 25.0, and 50.0 milligrams of the active ingredient for the symptomatic adjustment of the dosage to the patient to be treated. An effective amount of the drug is ordinarily supplied at a dosage level of from about 0.0002 mg/kg to about 50 mg/kg of body weight per day. The range is more particularly from about 0.001 mg/kg to 7 mg/kg of body weight per day.

Advantageously, the active agent of the present invention may be administered in a single daily dose, or the total daily dosage may be administered in dividend doses of two, three or four times daily.

For the treatment of acne vulgaris, androgenic alopecia, male pattern baldness, seborrhea, female hirsutism, benign prostatic hyperplasia, and prostatitis, the compounds of the instant invention can be combined with a therapeutically effective amount of another 5α-reductase inhibitor, such as finasteride or epristeride, or other 5α-reductase inhibitor compounds having type 2 activity, type 1 activity or dual activity for both isozymes, in a single oral, systemic, or parenteral pharmaceutical dosage formulation. Alternatively, a combined therapy can be employed wherein the compound of formula I and the other 5α-reductase inhibitor are administered in separate oral, systemic, or parenteral dosage formulations. Also, for the skin and scalp related disorders of acne vulgaris, androgenic alopecia, male pattern baldness, seborrhea, and female hirsutism, the compounds of the instant invention and another 5α-reductase inhibitor such as finasteride or epristeride can be formulated for topical administration. For example, a compound of formula I and finasteride can be administered in a single oral or topical dosage formulation, or each active agent can be administered in a separate dosage formulation, e.g., in separate oral dosage formulations, or an oral dosage formulation of finasteride in combination with a topical dosage formulation of a compound of formula I. See, e.g., U.S. Pat. Nos. 4,377,584 and 4,760,071 which describe dosages and formulations for 5α-reductase inhibitors.

Furthermore, administration of a compound of the present invention in combination with a therapeutically effective amount of a potassium channel opener, such as minoxidil, cromakalin, pinacidil, a compound selected from the classes of S-triazine, thiane-1-oxide, benzopyran, and pyridinopyran derivatives or a pharmaceutically acceptable salt thereof, may be used for the treatment of androgenic alopecia including male pattern baldness. Therapy may further comprise the administration of a 5α-reductase type 2 inhibitor such as finasteride or epristeride, or another 5α-reductase type 1 inhibitor, or a type 1 and type 2 dual inhibitor, in combination with a compound of the present invention and a potassium channel opener such as minoxidil. The active agents can be administered in a single topical dosage formulation, or each active agent can be administered in a separate dosage formulation, e.g., in separate topical dosage formulations, or an oral dosage formulation of a compound of formula I in combination with a topical dosage formulation of, e.g., minoxidil, or a single oral dosage formulation of a compound of formula I and another 5α-reductase inhibitor, in combination with a topical dosage formulation of, e.g., minoxidil. See, e.g., U.S. Pat. Nos. 4,596,812, 4,139,619 and WO 92/02225, published 20 Feb. 1992, for dosages and formulations of calcium channel openers.

Furthermore, for the treatment of acne vulgaris, a combined therapy can be used by administering a therapeutically effective amount of a compound of formula I in combination with a therapeutically effective amount of retinoic acid or a derivative thereof, e.g. an ester or amide derivative thereof, such as e.g., tretinoin or isotretinoin. Optionally, this combined therapy for acne vulgaris may further include a 5α-reductase type 2 inhibitor such as finasteride or epristeride, or a 5α-reductase type 1 inhibitor, or a dual type 1 and type 2 inhibitory compound. Other therapy for acne vulgaris may include a compound of formula I in combination with benzoyl peroxide or an antibacterial agent such as tetracycline.

Also, for the treatment of benign prostatic hyperplasia, a combined therapy comprising a administration of a compound of formula I with a 5α-reductase type 2 inhibitor, such as e.g., finasteride, and an alpha-1 adrenergic receptor antagonist, such as e.g., terazosin, doxazosin, prazosin, bunazosin, indoramin or alfuzosin, may be employed. More particularly, the combined therapy can comprise administering a compound of formula I with a 5α-reductase type 2 inhibitor, such as e.g., finasteride, and an alpha-$1_a$ adrenergic receptor antagonist (formerly called an alpha-$1_c$ adrenergic receptor antagonist). Compounds which are useful as alpha-$1_a$ adrenergic receptor antagonists can be identified according to procedures known to those of ordinary skill in the art, for example, as described in PCT/US93/09187 (WO94/

08040, published Apr. 14, 1994); PCT/US94/03852 (WO 94/22829, published Oct. 13, 1994); PCT/US94/10162 (WO 95/07075, published Mar. 16, 1995), and U.S. Pat. No. 5,403,847.

Also, for the treatment of acne vulgaris, androgenic alopecia, seborrhea, female hirsutism, benign prostatic hyperplasia, prostatitis and the prevention and/or treatment of prostatic cancer, a combined therapy can be used by administering a therapeutically effective amount of a compound of formula I with a therapeutically effective amount of an anti-androgen, such as, e.g., flutamide, spironolactone or casodex.

For combination treatment with more than one active agent, where the active agents are in separate dosage formulations, the active agents can be administered concurrently, or they each can be administered at separately staggered times.

The compounds of the present invention may be used in the preparation of a medicament useful for the treatment of hyperandrogenic disorders including acne vulgaris, androgenic alopecia, seborrhea, female hirsutism, benign prostatic hyperplasia, prostatitis and of prostatic cancer. The compounds of the present invention may also be used in the preparation of a medicament useful in the prevention of prostatic cancer.

The compounds of the present invention can be prepared readily according to the following Schemes and Examples or modifications thereof using readily available starting materials, reagents and conventional synthesis procedures. In these reactions, it is also possible to make use of variants which are themselves known to those of ordinary skill in this art, but are not mentioned in greater detail.

The compounds of this invention can be prepared as shown in Scheme 1.

SCHEME 1

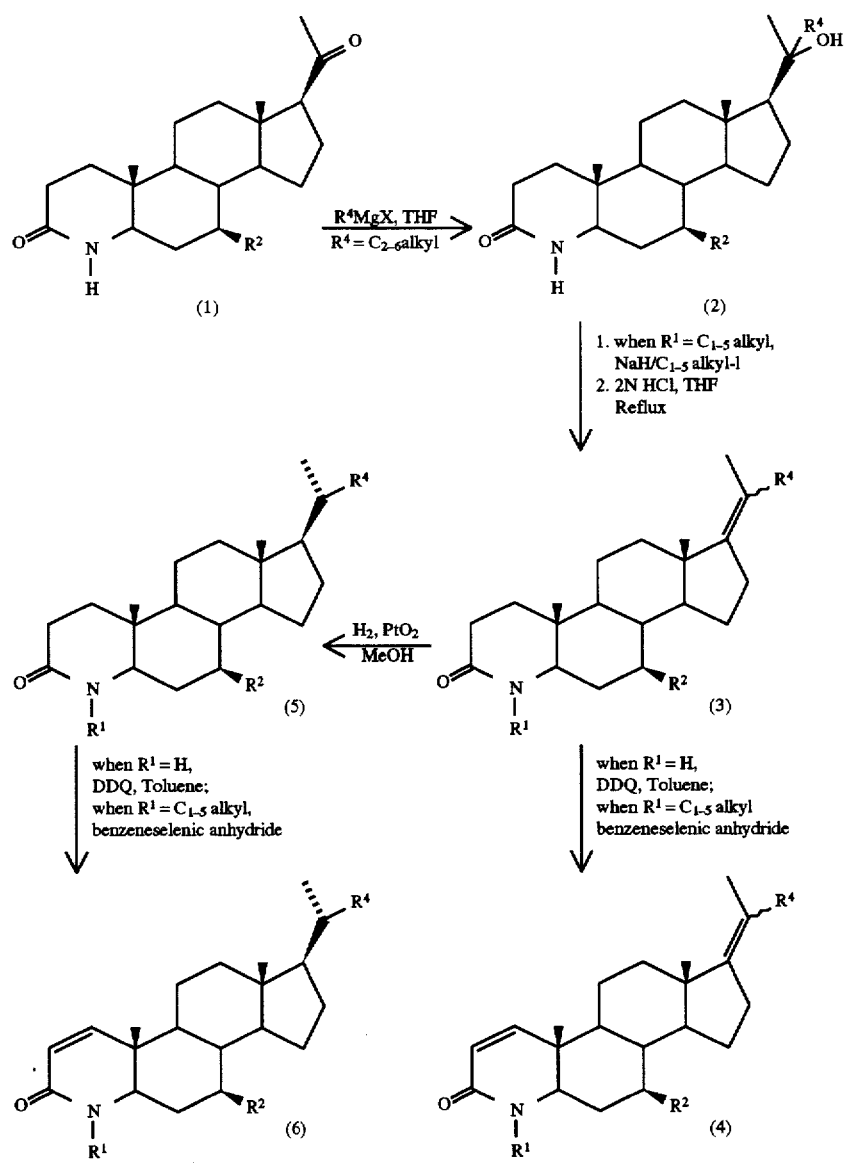

Starting with commercially available pregnenolone acetate, the appropriately 7-substituted derivative is prepared according to the procedures of PCT publication WO 93/23420 and to produce (1), the 7β-alkyl-substituted pregnenolone acetate. Treating (1) with the appropriate $C_{2-6}$alkyl Grignard in tetrahydrofuran (THF), produces the tertiary carbinol (2). The tertiary carbinol (2) may be alkylated at the 4-position by treatment with sodium hydride and the appropriate $C_{1-5}$alkyl iodide in a polar aprotic solvent such as THF or dimethylformamide (DMF). The 4-NH or 4-N-alkyl compound is then dehydrated in the presence of acid, for example, HCl or acetic acid, in a solvent such as THF or alcohol to produce the 17-ene (3). The 17-ene (3), in turn, may be dehydrogenated to form the 1,17-diene (4) by treatment with DDQ in toluene or benzeneselenic anhydride in chlorobenzene, or other known methods, for example as described in U.S. Pat. Nos. 5,084,574 and 5,021,571. DDQ is preferred for 4-NH compounds and benzeneselenic anhydride is preferred for 4-N-alkyl compounds.

Alternatively, the 17-ene (3) may be hydrogenated in the presence of a hydrogenation catalyst, for example $PtO_2$, Pd/C, rhodium on alumina, preferably $PtO_2$, in an appropriate solvent such as an alcohol or acetic acid, preferably methanol, to form the 17-alkyl derivative (5). The 17-alkyl derivative (5), in turn, may be dehydrogenated to form the 1-ene (6) by treatment with DDQ in toluene or benzeneselenic anhydride in chlorobenzene, as described above.

The desired 4-N-alkyl substitution may be effected as described previously by treating (2) with the appropriate alkyl iodide, or alternative, the procedure may be carried through with the 4-NH compound, and following after the desired 17-substitution and optional insertion of the 1,2-double bond, the 4-NH compound may be alkylated to the desired 4-N-alkyl compound.

Processes for inserting the 1,2-double bond in a 3-oxo-4-azasteroid are described in U.S. Pat. Nos. 5,084,574 and 5,021,571. The formation of a 7-β bond is described in U.S. Pat. Nos. 4,220,775 5,237,064.

SCHEME 2

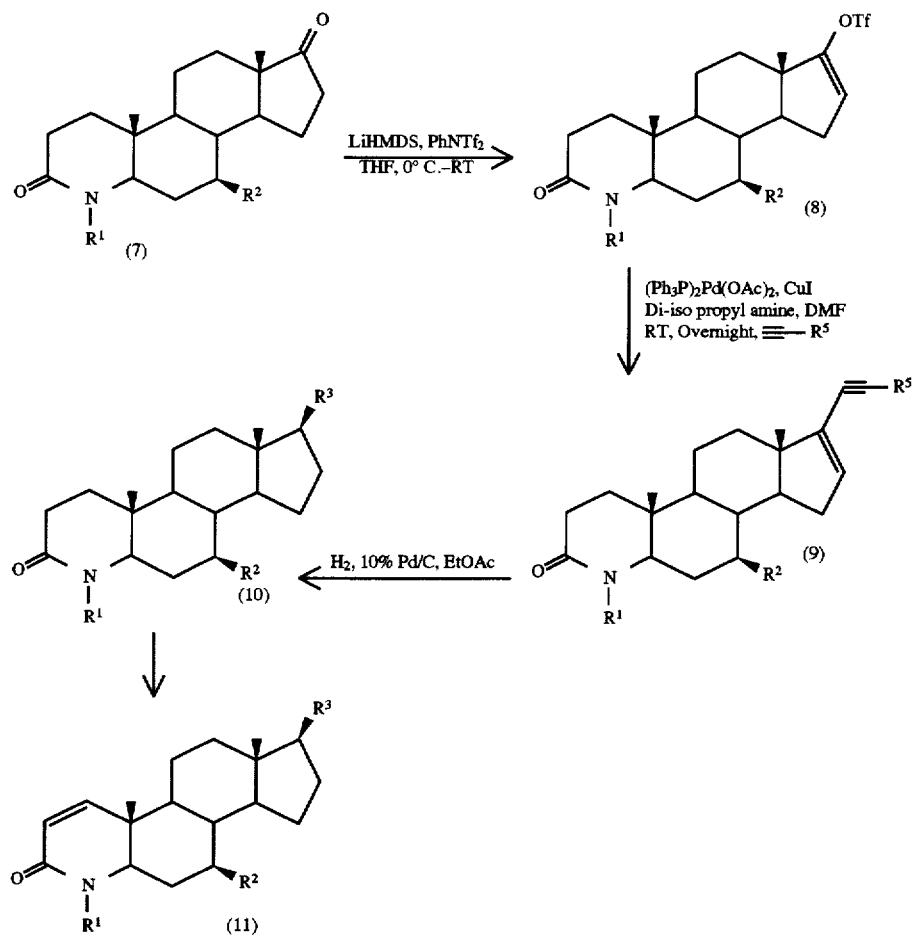

Alternatively, the compounds of the present invention may be prepared according to the procedures of Scheme 2. Compound (7), obtained according to procedures in WO 93/23420, is treated with N-phenyl trifluoro methane sulfonamide in a base such as lithium hexamethyldisilazide in THF to form the enol triflate (8). The enol triflate (8) is converted to the desired enyne (9) by treatment with di(triphenylphosphine)palladium diacetate or other appropriate $Pd_0$ catalyst with a catalytic amount of cuprous iodide and a mild base such as diisopropylamine or triethylamine in DMF with the appropriate alkyne. The enyne (9) is hyrdrogenated to produce the 17-alkyl derivative (10) by treating with $H_2$ in the presence of 10% Pd/C in an alcoholic or ethyl acetate solvent, preferably ethyl acetate. Insertion of the 1,2-double bond, if desired is accomplished as described in Scheme 1 to produce the 17-alkyl-1-ene (11).

The following examples are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus. Those skilled in the art will readily understand that known variations of the conditions and processes of the following preparative procedures can be used to prepare these compounds.

All temperatures given in the following examples are in degrees Celsius. $^1$H nuclear magnetic resonance (NMR) spectra were taken at 400 or 500 MHz at ambient temperature in the solvents indicated. Some abbreviations used herein are as follows: "DMF" is dimethylformamide; "EtOAc" is ethyl acetate; "Ph" is phenyl; "Tf" is —$SO_2CF_3$; "TFA" is trifluoroacetic acid; "THF" is tetrahydrofuran.

EXAMPLE 1

7β,20-Dimethyl-4-aza-5α-pregna-17-en-3-one

Step 1: 3-Acetoxy-pregn-5-en-20-ol

Sodium borohydride (21 gm) was added to a solution of pregnenolone acetate (100 g, 0.28 mol) in absolute ethanol (1 L) and methylene chloride (0.4 L) at −10° C. After stirring overnight at 4° C., another amount of sodium borohydride (10.5 gm) was added and the reaction stirred at room temperature overnight. The reaction mixture was quenched by pouring into 5% sodium phosphate monobasic (2 L) and extracted with methylene chloride. The organic extracts were dried over anhydrous magnesium sulfate and filtered through a pad of anhydrous sodium sulfate. The solvent was removed by rotoevaporation to give the title compound.

Step 2: 3-Acetoxy-20-tert-butyldimethylsilyloxy-pregn-5-ene

Imidazole (203.7 gm, 2.28 mol) was added to a stirred suspension of 3-acetoxy-pregn-5-en-20-ol (361 gm, 1 mol, product of Step 1) in dimethylformamide (3.7 L). t-Butyldimethylsilyl chloride (228.9 mg, 1.52 mol) was added over a 10–15 min period. The mixture was stirred at room temperature for 3 days. The dimethylformamide was removed by decantation and methanol (50 mL) was added to it. Water (4 L) was added and the solution extracted with ethyl acetate (2×4 L). The precipitate remaining behind after decantation was dissolved in ethyl acetate and added to the above ethyl acetate extracts. The combined solvent extracts were washed with water, saturated salt solution, and dried over anhydrous magnesium sulfate. The solvent was removed by rotoevaporation and the product purified by column chromatography on silica gel eluted with 2:1 hexane-methylene chloride followed by 1:1 hexane-methylene chloride. The title compound was isolated as a mixture of 20α- and β-isomers.

Step 3: 3-Acetoxy-20-tert-butyldimethylsilyloxy-pregn-5-en-7-one

To a solution of 3-acetoxy-20-tert-butyldimethylsilyloxy-pregn-5-ene (337 gm, 0.71 mol, product of Step 2) in methyl ethyl ketone (4 L) was added N-hydroxyphthalimide (115.8 gm, 0.71 mol) and dibenzoyl peroxide (1.1 gm, 4.4 mmol). Air was bubbled through the reaction as the reaction was refluxed for 7.5 hr. Additional N-hydroxyphthalimide (9 gm) and dibenzoyl peroxide (0.1 gm) were added and reflux continued for 5 hr. The solvent was removed by rotoevaporation and methylene chloride (0.7 L) was added and warmned to 40° C. Upon cooling to room temperature, the suspension was filtered and the filtrate washed with methylene chloride (0.2 L). The filtrate was rotoevaporated and treated with pyridine (1.35 L) and acetic anhydride (135 mL). After stirring overnight, the solvent was removed by rotoevaporation and the dark orange oil dissolved in methanol (0.6 L). The mixture was heated to 50° C. and then cooled to room temperature. The solution was allowed to stand for 3 days and then cooled in an ice bath. The precipitate was filtered, washed with methanol, and dried to yield the title compound. The filtrate was rotoevaporated to a dry gum to yield the crude product.

Step 4: 20-tert-Butyldimethylsilyloxy-7-methyl-pregn-5-ene-3,7-diol

A solution of 3-acetoxy-20-tert-butyldimethylsilyloxy-pregn-5-en-7-one (279 gm, 0.57 mol, product of Step 3) in tetrahydrofuran (5.6 L) was cooled to 4° C. A 3M solution of methyl magnesium chloride in tetrahydrofuran (1.037 L, 3.1 mol) was added at such a rate as to keep the temperature ≦0° C. The ice bath was removed and the reaction allowed to warm to room temperature overnight. The reaction was cooled in an ice bath and quenched with a 20% solution of ammonium chloride (3 L). The organic layer was removed and the aqueous layer extracted with ethyl acetate. The organic layers were combined, washed with saturated salt solution, and dried over anhydrous magnesium sulfate. The solution was filtered through a pad of anhydrous sodium sulfate and the solvent removed by rotoevaporation to yield the title compound.

Step 5: 20-tert-Butyldimethylsilyloxy-7-methyl-pregn-4,6-dien-3-one

A solution of 20-tert-butyldimethylsilyloxy-7-methyl-pregn-5-ene-3,7-diol (298 gm, 0.59 mol, product of Step 4) in toluene (3 L) and cyclohexanone (1.03 L) was azeotroped to remove 750 mL of solvent. A solution of aluminum isopropoxide (121 gm) in toluene (620 mL) was added and the solution azeotroped to remove another 650 mL of solvent. A reflux condenser was added and the solution refluxed overnight. The solution was cooled to 40° C. and Supercell™ (125 gm) and water (125 mL) were added. After stirring for 10 min, the mixture was filtered and the solids washed with toluene (550 mL). The solvent was removed by rotoevaporation to yield a orange liquid which was purified by column chromatography on silica gel eluted with hexane, followed by 5–10% ethyl acetate in hexanes. The title compound was isolated as a mixture of 20α- and 20β-isomers.

Step 6: 20-tert-Butyldimethylsilyloxy-7β-methyl-pregn-4-en-3-one

A slurry of 5% palladium on carbon (7.12 gm) and benzyl alcohol (213 mL) in heptane (356 mL) was refluxed for 20 min. The mixture was cooled to 80° C. and a solution of 20-tert-butyldimethyl-silyloxy-7-methyl-pregn-4,6-dien-3-one (71.2 gm, 0.16 mol, product of Step 5) in heptane (427 mL) was added. The slurry was refluxed for 9.5 h. The reaction was cooled to room temperature and filtered through SOLKA FLOK filter aid which was subsequently washed with hexane. The filtrate was extracted with acetonitrile which was subsequently back-extracted with hexane. The heptane and hexane extracts were combined, washed with saturated sodium sulfate and saturated salt solutions, and dried over anhydrous magnesium sulfate. The solution was filtered through a pad of anhydrous sodium sulfate and the solvent removed by rotoevaporation. The title compound was purified by column chromatography on silica gel eluted with 7% ethyl acetate in hexanes.

Step 7: 20-tert-Butyldimethylsilyloxy-7β-methyl-5-oxo-A-nor-3,5-secopregnan-3-oic acid To a solution of 20-tert-butyldimethylsilyloxy-7β-methyl-pregn-4-en-3-one (73.57 gm, 0.165 mol, product of Step 6)

in tert-butanol (0.96 L) was added a solution of sodium carbonate (25.8 gm) in water (120 mL). The mixture was heated to 80° C. with stirring. A warm solution of sodium periodate (244 gm) and potassium permanganate (1.91 gin) in water (0.96 L) was slowly added and then the reaction refluxed for 2 h. The reaction was cooled to room temperature and filtered through a pad of SuperCell™. The filter cake was washed with water (2×190 mL). The combined filtrates were rotoevaporated to remove the tert-butanol and washed with methylene chloride. The aqueous solution was acidified to pH ~3 with 2N hydrochloric acid and extracted with methylene chloride (3×). The organic extracts were combined, washed with 5% sodium bisulfite solution and saturated salt solution, and dried over anhydrous magnesium sulfate. The solvent was removed by rotoevaporation to yield the title compound as a white foam.

Step 8  20-tert-Butyldimethylsilyloxy-7β-methyl-4-azapregn-5-ene

To a solution of 20-tert-butyldimethylsilyloxy-7β-methyl-5-oxo-A-nor-3,5-secopregnan-3-oic acid (26 gm., 56 mmol, product of Step 7) in ethylene glycol (500 mL) under nitrogen was added anhydrous ammonium acetate (50 gm). The mixture was heated at 180° C. for 5 h, cooled to room temperature, and diluted with water (3.5 L). After stirring for 1 hr, the solid was filtered and the aqueous layer was extracted with methylene chloride (500 mL). The organic layer was dried over anhydrous magnesium sulfate and the solvent removed by rotoevaporation. The residue was combined with the filtered solid and dried in a vacuum oven overnight to give the title compound.

Step 9  20-tert-Butyldimethylsilyloxy-7β-methyl-5α-4-azapregnane

To a solution of 20-tert-butyldimethylsilyloxy-7β-methyl-4-azapregn-5-ene (23.9 g, 53.6 mmol, product of Step 8) in acetic acid (250 mL) was added platinum oxide (1.8 gm). The mixture was stirred overnight under hydrogen (1 atmosphere). The reaction mixture was filtered through a pad of Celite™ filter aid (trademark for diatomaceous earth) and the filtrate was coevaporated with toluene (3×500 mL) to remove all of the acetic acid. The residue was dissolved in chloroform and filtered again through a pad of Celite™ filter aid to remove residual catalyst. The solvent was removed by roto-evaporation to yield the title compound which was taken directly on to the next step without any further purification.

Step 10  20-Hydroxy-7β-methyl-5α-4-azapregnan-3-one

To a slurry of crude 20-tert-butyldimethylsilyloxy-7β-methyl-5α-4-azapregnane (25.2 g, product of Step 9) in acetonitrile (300 mL) was added an aqueous solution of hydrofluoric acid (12 mL). After stirring for 8 hr at room temperature, the reaction mixture was cooled to 0° C. and saturated sodium bicarbonate solution was slowly added. The mixture was extracted with methylene chloride (3×500 mL) and the combined extracts washed with water, saturated salt solution and dried over anhydrous sodium sulfate. The solvent was removed by rotoevaporation to give the title compound which was used without purification in the subsequent reaction.

Step 11:  7β-Methyl-5α-4-azapregnane-3,20-dione

To a stirred solution of 20-hydroxy-7β-methyl-5α-4-azapregnan-3-one (22.3 gms, 67 mmol, product of Step 10) in dry methylene chloride under nitrogen (110 mL) was added 4-methyl morpholine N-oxide (11.8 gms, 100 mmol) followed by 4Å molecular sieves (33 gm). To this mixture was added tetrapropylammonium perruthenate (1.2 gm). After stirring at room temperature for 4 h, the reaction mixture was poured through pad of silica gel in a 300 mL sintered glass funnel which was subsequently eluted with 4:1 ethyl acetate/methylene chloride (5 L). The solvent was removed by rotoevaporation and the title compound recrystallized.

Step 12:  20-Hydroxy-7β,20-dimethyl-4-aza-5α-pregnan-3-one

To a solution of 7β-methyl-4-aza-5α-pregnane-3,20-dione (1.24 g., 3.73 mmol., product of Step 11) in tetrahydrofuran (20 mL.) was added methylmagnesiumbromide in diethyl ether (3.73 mL., 11.2 mmol) at room temperature. The reaction was stirred for 45 minutes under a nitrogen atmosphere and then quenched with saturated ammonium chloride solution and diluted with ethyl acetate (500 mL.). The organic phase was washed with water (500 mL,×2) and brine solution (300 mL.). It was dried over sodium sulfate, filtered and the solvent evaporated in vacuo to give a white foam. The foam was flash chromatographed on silica gel using methanol in methylene chloride (1:19) as the mobile phase to yield a white foam. The foam was then recrystallized in methylene chloride and hexane (1:4) to yield the titled compound as white crystals. Rf=0.35, 5% methanol: methylene chloride. 400 MHz $^1$H NMR (CDCl$_3$): δ0.82 (s, 3H); 0.87 (s, 3H); 1.16(s, 3H); 1.27 (s, 3H); 3.04 (dd, 1H).

Step 13:  7β, 20-Dimethyl-4-aza-5α-pregn-17-en-3-one

A mixture of 20-Hydroxy-7β-methyl-4-aza-5α-pregnan-3-one (0.810 g., 2.35 mmol, product of Step 12), 2M hydrochloric acid (35 mL.) and tetrahydrofuran (THF, 35 mL) was refluxed at 70° C. for 3 hours. THF was then evaporated in vacuo and the aqueous phase was basified using 2.5M sodium hydroxide. The aqueous phase was then extracted with methylene chloride (200 mL) three times. The organic phases were combined and washed water (500 mL.) and brine (300 mL.). The organic phase was then dried with sodium sulfate, filtered and the solvent evaporated in vacuo to give a yellow oil. The oil was recrystallized in methylene chloride and hexane (1:3) to give a yellow solid.

EXAMPLE 2

7β,20-dimethyl-4-aza-5α-pregnan-3-one

To a solution of 7β,20-dimethyl-4-aza-5α-pregna-17-en-3-one (730 mg., 2.22 mmol, the product of Example 1) and methanol (40 mL) was added platinum oxide (250 mg). This mixture was stirred under a hydrogen atmosphere overnight. It was then filtered through Celite™ diatomaceous earth and the solvent was removed under vacuum. The crude residue was chromatographed using 10 % 2-propanol in hexane as the mobile phase to yield the titled compound as a white solid. 400 MHz $^1$H NMR (CDCl$_3$): δ0.66 (s, 3H); 0.83 (d, 3H); 0.85 (s, 3H); 0.91 (d, 3H); 0.99 (d, 3H); 3.05 (dd, 1H). Mass spec.=332 (M+1).

EXAMPLE 3

7β,20-dimethyl-4-aza-5αpregn-1-en-3-one

To a solution of 7β,20-dimethyl-4-aza-5α-pregna-3-one (500 mg., 1.51 mmol, the product of Example 2) in dry toluene (15 mL.) was added 2,3-dichloro-5,6-dicyano-1,4-benzoquinone (410 mg, 1.81 mmol), bis(trimethyl silyl) trifluoroacetamide (1.6 mL, 6.04 mmol) and triflic acid (0.00625 mL., 0.068 mmol). The mixture was stirred under nitrogen atmosphere overnight, followed by addition of methyl acetoacetate 90.032 mL., 0.30 mmol). The mixture was then refluxed overnight. The reaction mixture was poured into water (100 mL) containing sodium bicarbonate (800 mg.) and sodium sulfite (300 mg) and extracted with methylene chloride (3×100 mL). The organic phases were combined and washed with water (200 mL) and brine (100 mL). The organic phase was dried over sodium sulfate, filtered and the solvent evaporated in vacuo. The residue was purified by flash chromatography on silica gel eluded with 15% acetone in methylene chloride and recrystallization methyl ethyl ketone (MEK) to yield titled compound. 400 MHz $^1$H NMR (CDCl$_3$): δ0.67 (s, 3H); 0.82 (d, 3H); 0.89 (s, 3H); 0.92 (d, 3H); 1.01 (d, 3H); 3.34 (dd, 1H); 5.78 (dd, 1H); 6.78 (d, 1H). Mass spec.=330 (M+1).

EXAMPLE 4

7β,20-dimethyl-4-aza-5α-pregn-1,17-dien-3-one

The titled compound was synthesized in the same fashion as 7β,20-dimethyl-4-aza-5a-pregna-1-ene-3-one, starting with 7β,20-dimethyl-4-aza-5α-pregna-17-en-3-one with the exception it was purified by recrystallization in ethyl acetate. 400 MHz $^1$H NMR (CDCl$_3$): δ0.85 (s, 3H); 0.90 (s, 3H); 1.04 (d, 3H); 1.54 (s, 3H); 1.68 (s, 3H); 3.34 (dd, 1H); 5.78 (dd, 1H); 6.78 (d, 1H). Mass spec.=328 (M+1).

EXAMPLE 5

20-ethyl4,7β-dimethyl-4-aza-5α-pregn-17-en-3-one

Step 1: Preparation of 20-Ethyl-20-hydroxy-7β-methyl-4-aza-5α-pregnan-3-one

The titled compound was synthesized in a similar fashion to 20-Hydroxy-7β,20-dimethyl-4-aza-5α-pregnane-3-one using 3M ethylmagnesium bromide in diethyl ether in place of the methylmagnesium bromide. 400 MHz $^1$H NMR (CDCl$_3$): β0.82 (s, 3H); 0.84 (t, 3H); 0.86 (s, 3H); 0.99 (d, 3H); 1.23 (s, 3H); 3.03 (dd, 1H). Mass spec.=343 (M-18).

Step 2: Preparation of 20-Ethyl-20-hydroxy-4,7β-dimethyl-4-aza-5α-pregnan-3-one

To a slurry of sodium hydride (8.0 mg., 0.2 mmol) and 20-Ethyl-20-hydroxy-7β-methyl-4-aza-5α-pregnan-3-one (63.0 mg., 0.17 mmol, product of Step 1) in tetrahydrofuran was added methyl iodide (15.0 μL., 2.55 mmol). The solution was allowed to stir under a nitrogen atmosphere at room temperature overnight. The reaction was quenched with water and extracted with ethyl acetate (2×100 mL.). The organic phase was washed with water (100 mL) and brine (100 mL) and dried over sodium sulfate. The solvent was evaporated in vacuo and the residue purified via flash chromatography on silica gel eluding with 10 % acetone in methylene chloride to yield the titled compound as a white foam. 400 MHz $^1$H NMR (CDCl$_3$): δ0.81–0.84 (t, 3H); .083 (s, 3H); 0.85 (s, 3H); 1.03 (d, 3H); 1.22 (s, 3H); 2.9 (s, 3H); 2.99 (dd, 1H). Mass spec.=375 (M+).

Step 3: 20-ethyl-4,7β-dimethyl-4-aza-5β-pregn- 17-en-3-one

The titled compound was synthesized in a similar fashion to 7β,20-dimethyl-4-aza-5α-pregna-17-ene-3-one and taken forward without any purification.

EXAMPLE 6

20-ethyl-4,7β-dimethyl-4-aza-5α-pregnan-3-one

The titled compound was synthesized in a similar fashion to 7β,20-dimethyl-4-aza-5α-pregnane-3-one, starting with the product of Example 5. 400 MHz $^1$H NMR (CDCl$_3$): δ0.64 (d, 3H); 0.79 (d, 3H); 0.83 (s, 3H); 0.88 (d, 3H); 1.04 (d, 3H); 2.89 (s, 3H); 3.0 (dd, 1H). Mass spec.=359 (M+).

EXAMPLE 7

20-propyl -4,7β-dimethyl -4-aza-5α-pregnan-3 -one

Step 1: 20-Allyl-20-hydroxy-7β-methyl-4-aza-5α-pregnan-3-one

The titled compound was synthesized in a similar fashion to 20-Hydroxy-7β,20-dimethyl-4-aza-5α-pregnan-3-one using 2M allylmagnesium chloride in tetrahydrofuran in place of the methylmagnesium bromide. No further purification was done prior to the following step.

Step 2: 20-Allyl-20-hydroxy-4,7β-dimethyl-4-aza-5α-pregnan-3-one

The titled compound was synthesized in a fashion similar to 20-ethyl-20-Hydroxy-4,7β-dimethyl-4-aza-5α-pregnan-3-one. 400 MHz $^1$H NMR (CDCl$_3$): δ0.82 (s, 3H); 0.85 (s, 3H); 1.03 (d, 3H); 1.26 (s, 3H);2.89 (s,3H); 3.00 (dd, IH); 5.05 (dd, 2H); 5.78 (m, 1H).

Step 3: 20-propyl-4,7β-dimethyl-4-aza-5α-pregnan-3-one

A slurry of 20-allyl-20-Hydroxy-4,7β-dimethyl-4-aza-5α-pregnan-3-one (29.0 mg., 0.075 mmol), 10% palladium on carbon (5.0 mg.) and a mixture of ethyl acetate-ethanol (5.0 mL., 1:1) was stirred for 48 hours under a hydrogen atmosphere at room temperature. The reaction was then filtered through Celite™ and the solvent evaporated in vacuo. The residue was purified via HPLC on a Waters 19×300 mm 8μ silica Nova Pak column using a 5 to 10% 2-propanol/hexane linear gradient at a 20 mL. per minute flow rate to yield the titled compound. 400 MHz $^1$ H NMR (CDCl$_3$): δ0.65 (s, 3H); 0.80 (m, 9H); 1.02 (d, 3H); 2.89 (s, 3H); 3.00 (dd, 1H). Mass spec.=373 (M+).

EXAMPLE 8

Oral Composition

As a specific embodiment of an oral composition of a ompound of this invention, 5 mg 7β,20-dimethyl-4-aza-5α-pregna-1-en-3-one, is formulated with sufficient finely divided lactose to provide a total amount of 580 to 590 mg to fill a size 0 hard gelatin capsule.

Biological Assays

Preparation of Human prostatic and scalp 5α-reductases

Samples of human tissue were pulverized using a freezer mill and homogenized in 40 mM potassium phosphate, pH 6.5, 5 mM magnesium sulfate, 25 mM potassium chloride, 1 mM phenylmethylsulfonyl fluoride, 1 mM dithiothreitol (DTT) containing 0.25M sucrose using a Potter-Elvehjem homogenizer. A crude nuclear pellet was prepared by centrifugation of the homogenate at 1,500×g for 15 min. The crude nuclear pellet was washed two times and resuspended in two volumes of buffer. Glycerol was added to the resuspended pellet to a final concentration of 20%. The enzyme suspension was frozen in aliquots at −80° C. The prostatic and scalp reductases were stable for at least 4 months when stored under these conditions.

5α-reductase assay/Inhibitor studies

For IC$_{50}$ determinations, the inhibitors were dissolved in ethanol and serially diluted to the appropriate concentration. Human scalp or recombinantly-expressed enzyme can be used as the source of type 1 5α-reductase. Human prostate or recombinantly-expressed enzyme can be the source of type 2 5α-reductase. Typically, the type 1 enzyme was preincubated with inhibitor (0.1–1,000 nM) in 40 mM sodium phosphate, pH 7.0, 500 μM NADPH, 1 mM DTF and 1 mg/ML BSA for 18 h at 4° C. The reaction was initiated by the addition of [7- 3H]T (NEN, 20 Ci/mmol) and NADPH to fmal concentrations of 5 μM and 500 μM, respectively. The reaction was incubated at 37° C. for 90 min. Similarly, type 2 5α-reductase was preincubated with inhibitor (1–10,000 nM) in 40 mM sodium citrate, pH 5.5, 500 μM NADPH, 1 mM DTT and 1 mg/mL BSA for 18 h at 4° C. The reaction was initiated by the addition of [7-3H]T (NEN, 20 Ci/mmol) and NADPH to a final concentration of 0.3 μM and 500 μM, respectively. The conversion of T to DHT was monitored using a radioflow detector following separation by reverse phase HPLC (Whatman RACII C18 column, 1 mL/min 0.1% TFA in water:methanol (42:58); retention times T, 6.3 min, DHT, 9.7 min).

Representative compounds of the present invention assayed for 5α reductase inhibitory activity displayed an $IC_{50}$ for the type 1 enzyme below 1 μM. Compounds wherein the C1–C2 bond is a double bond and $R^1$ is hydrogen are time-dependent inhibitors active at low levels over time and having $IC_{50}$, less than 0.001 μM.

Human Dermal Papilla Cell Assay

The dermal papilla is a small group of cells at the base of each hair follicle, and it is presently thought that these cells are stem cells that form the basis for hair growth. These cells have been shown to have 5α reductase activity, and it is therefore possible to test inhibitors of 5α reductase in these cell culture systems.

Isolated and cultured dermal papilla cells are prepared according to the methods of Messenger, A. G., "The Culture of Dermal Papilla Cells From Human Hair Follicles," *Br. J. Dermatol.*, 110:685–689 (1984) and Itami, S. et al., "5α-Reductase Activity In Cultured Human Dermal Papilla Cells From Beard Compared With Reticular Dermal Fibroblasts," *J. Invest. Dermatol.*, 94:150–152 (1990). Beard dermal papilla cells and occipital scalp hair of two different individuals are used throughout the study. All experiments are performed at confluency after the fourth to sixth subculture.

Confluent monolayers are rinsed twice with phosphate-buffered saline, scraped from dishes by rubber policemen, and collected into a centrifuge tube. The cell suspensions are centrifuged at 1,500 rpm for 10 min. at 4° C. The pellets are resuspended in 20 mM Tris-HCl buffer, pH 7.5, at 4° C., containing 250 mM sucrose, 1 mM $MgCl_2$, and 2 mM $CaCl_2$, by vortexing and 10 passes through a 25-gauge needle. The crude homogenate is further homogenized by a teflon-glass homogenizer, and is used as the cell homogenate. For the study of subcellular localization of 5α-reductase, the cell homogenate is centrifuged at 800×g for 10 min. to yield a crude nuclear pellet.

The resultant supernatant is centrifuged at 10,000×g for 15 min. to produce a crude mitochondrial pellet. The supernatant is centrifuged at 100,000×g for 60 min. to yield a microsomal pellet and cytosol. Each particulate fraction is washed twice and resuspended in the buffer.

A standard incubation mixture will consist of 50 nM [$^3$H]-testosterone, 1 mM NADPH, 100 mM sodium citrate, pH 5.5 or 100 mM Tris-HCl, pH 7.5, and 50 mL of the cell homogenate, in a final volume of 100 mL. Each tube contains 50–100 mg of cellular protein. Incubation is carried out at 37° C. for 30 min. During this incubation, the reaction is proportional to the time. For the study of optimum pH, citrate buffer is used at pH 4.5–6.5, and the Tris HCl buffer at pH 7.0–9.0. The protein content is determined by the method of Lowry, et al., "Protein Measurement With The Folin Phenol Reagent," *J. Biol. Chem.*, 193:265–275 (1951).

After incubation, the reaction is stopped by adding 4 times volume of chloroform-methanol (2/1 :V/V) containing 110 mg each of carrier steroids. The extracted steroids are analyzed by thin-layer chromatography as previously described by Gomez, et al., "In Vitro Metabolism Of Testosterone-4-$^{14}$C and D-androstene-3, 17-dione-4-$^{14}$C In Human Skin.," *Biochem.*, 7:24–32 (1968), and the purity of each steroid is determined by the recrystallization method. The activity of 5α-reductase is expressed by the sum of dihydrotestosterone, androstanediol and androstanedione formed. [1,2-$^3$H]-testosterone (55.2 Ci/mmol) is obtainable from New England Nuclear Corporation (Boston, Mass.) and unlabeled steroids can be purchased from Sigma Chemical Company (St. Louis, Mo.). Fetal calf serum is obtainable from Hazleton (Lenaxa, Kans.). All other chemicals are of reagent grade.

The following describes an example of methodology that can be used for detection of hair growth.

MACROPHOTOGRAPHY AND GLOBAL PHOTOGRAPHY PROCEDURE FOR DETECTION OF HAIR GROWTH

A. Macrophotographic Procedure

Location: ID card Haircount target area

Equipment: Film: Kodak-T-max 24 exposure each of same emulsion lot number

Camera: Nikon N-6000

Lens: Nikkor 60 mm f2.8

Flashes: Nikon SB-21B Macroflash

Device: registration device

Photographic Procedure:

In these clinical photographs, the only variable allowed is the haircount. Film emulsion, lighting, framing, exposure, and reproduction ratios are held constant.

1. The haircount area on the patient is prepared as follows: A small (~1 mm) dot tattoo is placed at the beginning of the study at the leading edge of the bald area directly anterior to the center of the vertex bald spot, using a commercial tattooing machine or manually (needle and ink). An area approximately one square inch in size, centered at the tattoo at the leading edge of the balding area, is clipped short (~2 mm). Cut hairs are removed from the area to be photographed, using tape. Compressed air and/or ethanol wipes may also be used to facilitate removal of cut hairs.
2. Magnification: Each lens supplied has a fixed reproduction ratio of 1:1.2. Aperture: Every photograph is taken at f/22. Film: T-Max 100 (24 exposure) is used.
3. Patient's haircount target area. Three exposures (−⅔, 0, and +⅔f-stop).

A trained technician places a transparency over the photographic print and, using a felt tip pen, places a black dot over each visible hair. The dot map transparency is then counted using image analysis with computer assistance.

Photographs are coded with a random number corresponding to study site, visit number and patient allocation number to insure blinding to time. At Month 6, baseline and Month 6 photographs are counted and data analyzed for interim analysis. At Month 12, baseline, Month 6 and Month 12 photographs are counted and data analyzed for the primary endpoint.

Methodology for detection of hair growth is also described in Olsen, E. A. and DeLong, E., *J. American Academy of Dermatology*, Vol. 23, p. 470 (1990).

B. Global Photographic Procedure

Locations: Color card/patient Id Global photograph

Equipment: Film: Kodachrome KR-64 24 exposure each of same emulsion lot number

Camera: Nikon N-6000

Lens: Nikkor 60 mm f2.8

Flashes: Nikon SB-23

Photographic Procedure

In these clinical photographs, the only variable allowed is the global area's appearance. Anything extraneous to the area (clothing, furniture, walls, etc.) is eliminated from the fields to be photographed.

What is claimed is:

1. A compound of structural formula I:

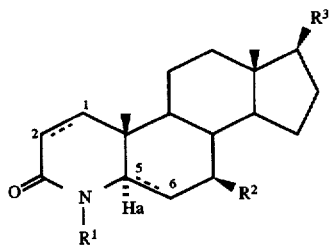

or a pharmaceutically acceptable salt or stereoisomer thereof wherein:

wherein:

the C1–C2 and C5–C6 bonds designated with a dotted line each independently represent a single or double bond, provided that when the C5–C6 is a double bond, $H_a$ is absent and when the C5–C6 bond is a single bond $H_a$ is present and represents hydrogen;

$R^1$ is selected from hydrogen and $C_{1-5}$ alkyl;

$R^2$ is $C_{1-5}$alkyl, either straight or branched chain; and $R^3$ is $C_{3-7}$alkyl, either straight or branched chain, optionally having one degree of unsaturation.

2. A compound of claim 1 wherein: the C5–C6 bond is a single bond and $H_a$ is present.

3. A compound of claim 2 wherein: $R^2$ is methyl.

4. The compound of claim 1 selected from the group consisting of:

(1) 7β,20-dimethyl-4-aza-5α-pregn-17-en-3-one,
(2) 7β,20-dimethyl-4-aza-5α-pregn-1,17-dien-3-one,
(3) 20-ethyl-4,7β-dimethyl-4-aza-5α-pregn-17-en-3-one,
(4) 20-ethyl-4,7β-dimethyl-4-aza-5α-pregnan-3-one,
(5) 7β,20-dimethyl-4-aza-5α-pregnan-3-one,
(6) 7β,20-dimethyl-4-aza-5α-pregn-1-en-3-one,
(7) 20-ethyl-4,7β-dimethyl-4-aza-5α-pregnan-3-one,
(8) 20-propyl-4,7β-dimethyl-4-aza-5α-pregnan-3-one,
(9) 20-ethyl-4,7β-dimethyl-4-aza-5α-pregn-1-en-3-one,
(10) 4,7β,20-trimethyl-4-aza-5α-pregn-1-en-3-one,
(11) 20-propyl-4,7β-dimethyl-4-aza-5α-pregn-1-en-3-one,
(12) 20-ethyl-7β-methyl-4-aza-5α-pregn-1-en-3-one,
(13) 20-propyl-7β-methyl-4-aza-5α-pregnan-3-one,
(14) 20-propyl-7β-methyl-4-aza-5α-pregn-1-en-3-one,
(15) 17β-n-propyl-7β-methyl-4-aza-5a-androst-1-en-3-one,
(16) 17β-n-propyl-4,7β-dimethyl-4-aza-5α-androst-1-en-3-one,
(17) 17β-isobutyl-7β-methyl-4-aza-5α-androst-1-en-3-one,
(18) 17β-n-butyl-7β-methyl-4-aza-5α-androst-1-en-3-one,
(19) 17β-tert.-butyl-7β-methyl-4-aza-5α-androst-1-en-3-one,
(20) 17β-n-butyl-4,7β-dimethyl-4-aza-5α-androst-1-en-3-one,
(21) 17β-isobutyl-4,7β-dimethyl-4-aza-5α-androst-1-en-3-one,
(22) 17β-n-pentyl-7β-methyl-4-aza-5α-androst-1-en-3-one,
(23) 17β-isopentyl-7β-methyl-4-aza-5α-androst-1-en-3-one,
(24) 17β-(5-methylhexyl)-7β-methyl-4-aza-5α-androst-1-en-3-one,
(25) 17β-(5-methylhexyl)-4,7β-dimethyl-4-aza-5β-androst-1-en-3-one,
(26) 17β-n-propyl-7β-methyl-4-aza-5α-androstan-3-one,
(27) 17β-n-propyl-4,7β-dimethyl-4-aza-5α-androstan-3-one,
(28) 17β-n-butyl-7β-methyl-4-aza-5α-androstan-3-one,
(29) 17β-n-butyl-4,7β-dimethyl-4-aza-5α-androstan-3-one,
(30) 17β-(5-methylhexyl)-7β-methyl-4-aza-5α-androstan-3-one, or
(31) 17β-(5-methylhexyl)-4,7β-dimethyl-4-aza-5α-androstan-3-one.

5. A compound of claim 1 wherein: the C1–C2 bond is a double bond and $R^1$ is hydrogen.

6. A compound of claim 1 wherein: $R^3$ is $C_{3-6}$ alkyl, optionally containing one degree of unsaturation.

7. A compound of claim 1 wherein $R^3$ is saturated.

8. A compound of claim 2 wherein: the C1–C2 bond is a double bond, $R^1$ is hydrogen, $R^2$ is methyl, and $R^3$ is $C_{3-6}$ alkyl.

9. A compound of claim 8 wherein: $R^3$ is saturated.

10. The compound of claim 1 which is: 7β,20-dimethyl-4-aza-5α-pregn-1-en-3-one.

11. A method for treating the hyperandrogenic condition of acne vulgaris comprising the step of administering to a human in need of such treatment a therapeutically effective amount of a compound of claim 1, alone or in combination with a therapeutically effective amount of finasteride.

12. A pharmaceutical composition comprising a pharmaceutically acceptable carrier and a therapeutically effective amount of a compound of claim 1 or a pharmaceutically acceptable salt thereof, alone or in combination with a therapeutically effective amount of finasteride.

* * * * *